US006815196B2

(12) United States Patent
Bathe et al.

(10) Patent No.: US 6,815,196 B2
(45) Date of Patent: Nov. 9, 2004

(54) NUCLEOTIDE SEQUENCES ENCODING O-SUCCINYLHOMOSERINE SULFHYDRYLASE

(75) Inventors: Brigitte Bathe, Salzkotten (DE); Walter Pfefferle, Halle (DE); Klaus Huthmacher, Gelnhausen (DE); Christian Rueckert, Guetersloh (DE); Joern Kalinowski, Bielefeld (DE); Alfred Puehler, Bielefeld (DE); Michael Binder, Steinhagen (DE); Dieter Greissinger, Niddatal (DE); Georg Thierbach, Bielefeld (DE)

(73) Assignee: Degussa AG, Duesseldorf (DE)

( * ) Notice: Subject to any disclaimer, the term of this patent is extended or adjusted under 35 U.S.C. 154(b) by 195 days.

(21) Appl. No.: 09/919,831

(22) Filed: Aug. 2, 2001

(65) Prior Publication Data

US 2002/0102664 A1 Aug. 1, 2002

Related U.S. Application Data

(60) Provisional application No. 60/294,224, filed on May 31, 2001.

(30) Foreign Application Priority Data

Sep. 2, 2000 (DE) .......................... 100 43 335
Feb. 28, 2001 (DE) .......................... 101 09 688

(51) Int. Cl.$^7$ ................................. C12N 1/20
(52) U.S. Cl. ..................... 435/252.33; 435/320.1; 536/23.1; 536/23.2; 536/23.7
(58) Field of Search .................. 536/23.2, 23.1, 536/23.7; 435/320.1, 252.33

(56) References Cited

U.S. PATENT DOCUMENTS

2002/0197605 A1 * 12/2002 Nakagawa et al. ............ 435/6

FOREIGN PATENT DOCUMENTS

| EP | 1 108 790 | 6/2001 |
|----|-----------|--------|
| WO | WO 01/00802 | 1/2001 |
| WO | WO 01 00842 | 1/2001 |
| WO | WO 01 00843 | 1/2001 |
| WO | WO 01/00844 | 1/2001 |
| WO | WO 01/00845 | 1/2001 |
| WO | WO 01/00847 | 1/2001 |

OTHER PUBLICATIONS

GenBank Accession No. AX065835. *Corynebacterium glutamicum* genes encoding proteins involved in homeostatis and adaptation. SEQ ID No.: 179 from WO 0100842. Jan., 2001.*

GenBank Accession No. AX063913. *Corynebacterium glutamicum* genes encoding metabolic pathway proteins. SEQ ID No.: 195 from WO 0100843. Jan., 2001.*

Johnston et al. GenBank Accession No. U00059. *Saccharomyces cerevisiae* chromosome VIII cosmid 8263. Published Sep. 4, 1997.*

Hwang et al. *Corynebacterium glutamicum* utilizes both transsulfuration and direct sulfhydrylation pathways for methionine biosynthsis. J Bacteriol. 2002 184(5): 1277–1286.*

Tate, R., et al.: "The Rhizobium Etli Metz Gene is Essential for Methionine Biosynthesis and Nodulation of Phaseolus Vulgaris"; Molecular Plant–Microbe Interactions, vol. 12, No. 1, pp. 24–35, Jan. 1999.

Lorenz, Eva, et al.: "MetR–Mediated Repression of the glyA Gene in *Escherichia coli*"; Fems Microbiology Letters, vol. 144, No. 2–3, pp. 229–233, 1996.

Hwang, B.J. et al; "Analysis of *Corynebacterium glutamicum* Methionine Biosynthetic Pathway: Isolation and Analysis of metB Encoding Cystathionine gamma–Synthase"; Mol. Cells, vol. 9, No. 3, pp. 300–308; Feb. 1999.

Park, S.D., et al; "Isolation and Analysis of metA, a Methionine Biosyntheitic Gene Encoding Homoserine Acetyltransferase in *Corynebacterium glutamicum*"; Molecules and Cells, vol. 8, No. 3, pp. 286–294; Jan. 1998.

Foglino, M. et al.; "A Direct Sulfhydrylation Pathway is Used for Methionine Biosynthesis in Pseudomonas Aeruginosa"; Microbiology, vol. 141, No. 2, pp. 431–439; Feb. 1995.

Fritsch, Paula, et al.; "Role of the RNA Polymerase Alpha Subunits in MetR–Dependent Activation of metE and metH: Important Residues in the C–Terminal Domain and Orientation Requirements within RNA Polymerase"; Journal of Bacteriology, vol. 182, No. 19, pp. 5539–5550; Oct. 2000.

* cited by examiner

*Primary Examiner*—Kathleen Kerr
(74) *Attorney, Agent, or Firm*—Oblon, Spivak, McClelland, Maier & Neustadt, P.C.

(57) ABSTRACT

The present invention relates to isolated polynucleotides from *Corynebacterium glutamicum* encoding proteins of the transcription activator (MetR) and O-succinylhomoserine sulfhydrylase (MetZ). The invention also relates to producing L-amino acids, particularly methionine, in coryneform cells having attenuated metR and metZ genes.

11 Claims, 1 Drawing Sheet

SEQUENCE LISTING

<160> NUMBER OF SEQ ID NOS: 8

<210> SEQ ID NO 1
<211> LENGTH: 2628
<212> TYPE: DNA
<213> ORGANISM: Corynebacterium glutamicum
<220> FEATURE:
<221> NAME/KEY: CDS
<222> LOCATION: (447)..(1013)
<223> OTHER INFORMATION:
<221> NAME/KEY: CDS
<222> LOCATION: (1038)..(2183)
<223> OTHER INFORMATION:

<400> SEQUENCE: 1

```
cggtcacgtt gggatcgttg tcaaaactcc ccagtggttt cacttcataa actcgcggag      60
ttttccgggg aactgaaaaa catcgtccga taggccagcg tctaattcag cagcgatttc     120
ggcagcaagc ccagcgccat taatcagagc ggtgaaataa acatggttca tgattatgtc     180
aggacggtaa ttagacttat gaccaggttt aaggaggtca ccaggttgaa gccgcgctat     240
tgttccgtgg aaaaggggc cctgatctag ctgattattc atcgcagtaa gcgctttcgg      300
taggtgggtg aatcatcgta gtcttccgag ccccgtgacc cgatccgttt tgtgcaatcc     360
aatgctactc ccacagagcg ggctactttc tctaaaaatg ttctcatagt agataaaatt     420
gttcttaaag cgacattatt gtctgc atg gaa gac gat ctc agt gct gct ctc     473
                              Met Glu Asp Asp Leu Ser Ala Ala Leu
                                1               5 gtc aaa gcg ctt ttc gac gcg cga acc caa cgc agg ctc tct atc tcg     521
Val Lys Ala Leu Phe Asp Ala Arg Thr Gln Arg Arg Leu Ser Ile Ser
 10              15                  20                  25 gcg tta gct gaa tcc tcc ggt gtg tcg cga gca atg att tcc cgc gtg     569
Ala Leu Ala Glu Ser Ser Gly Val Ser Arg Ala Met Ile Ser Arg Val
                 30                  35                  40 gaa aac gca gag gcg caa cca agc gct gca tta ctt gga cgc ctt tcc     617
Glu Asn Ala Glu Ala Gln Pro Ser Ala Ala Leu Leu Gly Arg Leu Ser
             45                  50                  55 ggt gca ttg ggt atg acg ctt tcg gag ctc att gca cag gct gaa ggt     665
Gly Ala Leu Gly Met Thr Leu Ser Glu Leu Ile Ala Gln Ala Glu Gly
         60                  65                  70 ggc tat gac cgg ggc gct cgg cgg tca aag cag tct gta tgg aca gat     713
Gly Tyr Asp Arg Gly Ala Arg Arg Ser Lys Gln Ser Val Trp Thr Asp
     75                  80                  85 cca gct acc ggt tac aca cgg cgt gca gtg tca cag ccg tca gaa tcc     761
Pro Ala Thr Gly Tyr Thr Arg Arg Ala Val Ser Gln Pro Ser Glu Ser
 90                  95                 100                 105 cca cta gaa cta gtg gaa gta atg ctg cct cct ggg gcg gaa gtt ggc     809
Pro Leu Glu Leu Val Glu Val Met Leu Pro Pro Gly Ala Glu Val Gly
                110                 115                 120 tac cca gct gat gct tat cgt ttc atg gat cag gtg gtc tgg gta ctc     857
Tyr Pro Ala Asp Ala Tyr Arg Phe Met Asp Gln Val Val Trp Val Leu
            125                 130                 135 gaa ggg gcc gtt cgt att act gaa ggt gaa gag gtc cac gaa ctt tca     905
Glu Gly Ala Val Arg Ile Thr Glu Gly Glu Glu Val His Glu Leu Ser
        140                 145                 150 acg ggg gat tgt cta cgg ttt ggg cct ccg cga gat acc gac ttt gct     953
Thr Gly Asp Cys Leu Arg Phe Gly Pro Pro Arg Asp Thr Asp Phe Ala
    155                 160                 165 aat ccc acc acc gta gcc act agg tat tta gtt gcc ttg gac aag cgt    1001
Asn Pro Thr Thr Val Ala Thr Arg Tyr Leu Val Ala Leu Asp Lys Arg
```

-continued

```
             170                 175                 180                 185
gta cct cgt gct tgatataaca agtaaggaag cctg atg aat ttt tac cca              1052
Val Pro Arg Ala                          Met Asn Phe Tyr Pro
                                         190 cca tct gta cct att aac cct gcg tgg cgt cca ccc aca gta act gtg             1100
Pro Ser Val Pro Ile Asn Pro Ala Trp Arg Pro Pro Thr Val Thr Val
195                 200                 205                 210 caa gcg gga cgg cca gcc aga act cct ggt gcg ccg atg aac cca cct             1148
Gln Ala Gly Arg Pro Ala Arg Thr Pro Gly Ala Pro Met Asn Pro Pro
                        215                 220                 225 atc acg ttg tcc agc act tat gtt cat gat tca gaa aaa gct tat ggg             1196
Ile Thr Leu Ser Ser Thr Tyr Val His Asp Ser Glu Lys Ala Tyr Gly
                230                 235                 240 cgc gat ggc aat gat gga tgg ggt gca ttt gag gct gcc atg gga act             1244
Arg Asp Gly Asn Asp Gly Trp Gly Ala Phe Glu Ala Ala Met Gly Thr
        245                 250                 255 cta gat ggt ggg ttc gcg gta tct tat tct tca ggt ttg gca gcg gca             1292
Leu Asp Gly Gly Phe Ala Val Ser Tyr Ser Ser Gly Leu Ala Ala Ala
260                 265                 270 acg tcg att gct gat ttg gtt cct act ggt ggc aca gtt gtt tta cct             1340
Thr Ser Ile Ala Asp Leu Val Pro Thr Gly Gly Thr Val Val Leu Pro
275                 280                 285                 290 aaa gct gcc tat tat ggc gtg acc aat att ttc gcc agg atg gaa gcc             1388
Lys Ala Ala Tyr Tyr Gly Val Thr Asn Ile Phe Ala Arg Met Glu Ala
                295                 300                 305 cgc gga agg ctg aag gtt cga act gtt gat gca gac aat acc gaa gaa             1436
Arg Gly Arg Leu Lys Val Arg Thr Val Asp Ala Asp Asn Thr Glu Glu
                310                 315                 320 gtg att gct gct gct caa ggt gca gat gtg gtg tgg gtg gaa tcg atc             1484
Val Ile Ala Ala Ala Gln Gly Ala Asp Val Val Trp Val Glu Ser Ile
        325                 330                 335 gct aat ccg acg atg gtg gta gct gat atc cct gca ata gtc gac ggt             1532
Ala Asn Pro Thr Met Val Val Ala Asp Ile Pro Ala Ile Val Asp Gly
        340                 345                 350 gtg cgt ggg ctt gga gtt ttg act gtc gtt gac gcg act ttc gca acg             1580
Val Arg Gly Leu Gly Val Leu Thr Val Val Asp Ala Thr Phe Ala Thr
355                 360                 365                 370 cca ctt cgt caa cgt cca ttg gaa ctt ggt gct gat att gtg ctt tac             1628
Pro Leu Arg Gln Arg Pro Leu Glu Leu Gly Ala Asp Ile Val Leu Tyr
                375                 380                 385 tcg gca acc aaa ctt atc ggt gga cac tct gat ctt ctt ctt gga gtc             1676
Ser Ala Thr Lys Leu Ile Gly Gly His Ser Asp Leu Leu Leu Gly Val
                390                 395                 400 gca gtg tgc aag tct gag cac cat gcg cag ttt ctt gcc act cac cgt             1724
Ala Val Cys Lys Ser Glu His His Ala Gln Phe Leu Ala Thr His Arg
        405                 410                 415 cat gat cat ggt tca gtg ccg gga ggt ctt gaa gcg ttt ctt gct ctc             1772
His Asp His Gly Ser Val Pro Gly Gly Leu Glu Ala Phe Leu Ala Leu
420                 425                 430 cgt gga ttg tat tcc ttg gcg gtg cgt ctt gat cga gca gaa tcc aac             1820
Arg Gly Leu Tyr Ser Leu Ala Val Arg Leu Asp Arg Ala Glu Ser Asn
435                 440                 445                 450 gca gca gaa ctt tcg cgg cga ctt aac gcg cat cct tcg gtt acc cgc             1868
Ala Ala Glu Leu Ser Arg Arg Leu Asn Ala His Pro Ser Val Thr Arg
                455                 460                 465 gtc aat tat cca gga ctt cct gat gat ccc caa cat gaa aaa gcc gtg             1916
Val Asn Tyr Pro Gly Leu Pro Asp Asp Pro Gln His Glu Lys Ala Val
                470                 475                 480 cga gtc cta ccc tct gga tgt gga aac atg ttg tca ttt gag ctt gat             1964
```

```
                                 Arg Val Leu Pro Ser Gly Cys Gly Asn Met Leu Ser Phe Glu Leu Asp
                                             485                 490                 495 gca aca cct gaa cga act gat gag att ctc gaa agc ctg tca ctt tta              2012
Ala Thr Pro Glu Arg Thr Asp Glu Ile Leu Glu Ser Leu Ser Leu Leu
        500                 505                 510 acc cac gcg acc agt tgg gga ggt gtg gaa aca gcc att gaa cgt cgc              2060
Thr His Ala Thr Ser Trp Gly Gly Val Glu Thr Ala Ile Glu Arg Arg
515                 520                 525                 530 acc agg cgg gat gct gaa gtg gtg gca gga gta ccg atg act ctt tgc              2108
Thr Arg Arg Asp Ala Glu Val Val Ala Gly Val Pro Met Thr Leu Cys
                535                 540                 545 cgc gtt tcc gta gga att gaa gac gtt gaa gat cta tgg gaa gac ctc              2156
Arg Val Ser Val Gly Ile Glu Asp Val Glu Asp Leu Trp Glu Asp Leu
            550                 555                 560 aac gcc tca atc gac aaa gtt ctg ggt tagaactcgt agccagtaac                    2203
Asn Ala Ser Ile Asp Lys Val Leu Gly
                565             570 cagaccttca gtgtttggtt gccactccag tgctggggcg acatgatcag cgaagttctt            2263
caggatcgac gcgttgatct caacacccat ttggttgggg gcggtgagca tcaaggtgtc            2323
ggcttccatc acagctttgt cttccttgag ctggtcgatg agttcatcgg acttccggc             2383 gtagctgcga ccgaacgtgg atcgggtatc atccaggatt cctacttggt caccgccttg            2443
tccctgaagt ccgaaaagct cacggtcgcg gtcggtgacg atcgggaaga tggacctgga            2503
gacagacaca cgtggggtcc aatcgtgtcc ggcttctttc caagcttggc ggtagaacgc            2563
gatttgatcg gcttgcagat ccccgaagga ttggccggtg gcttcggcga cgagggtgga            2623
gctca                                                                        2628
```

<210> SEQ ID NO 2
<211> LENGTH: 189
<212> TYPE: PRT
<213> ORGANISM: Corynebacterium glutamicum

<400> SEQUENCE: 2

```
Met Glu Asp Asp Leu Ser Ala Ala Leu Val Lys Ala Leu Phe Asp Ala
1               5                   10                  15

Arg Thr Gln Arg Arg Leu Ser Ile Ser Ala Leu Ala Glu Ser Ser Gly
            20                  25                  30

Val Ser Arg Ala Met Ile Ser Arg Val Glu Asn Ala Glu Ala Gln Pro
        35                  40                  45

Ser Ala Ala Leu Leu Gly Arg Leu Ser Gly Ala Leu Gly Met Thr Leu
    50                  55                  60

Ser Glu Leu Ile Ala Gln Ala Glu Gly Gly Tyr Asp Arg Gly Ala Arg
65                  70                  75                  80

Arg Ser Lys Gln Ser Val Trp Thr Asp Pro Ala Thr Gly Tyr Thr Arg
                85                  90                  95

Arg Ala Val Ser Gln Pro Ser Glu Ser Pro Leu Glu Leu Val Glu Val
            100                 105                 110

Met Leu Pro Pro Gly Ala Glu Val Gly Tyr Pro Ala Asp Ala Tyr Arg
        115                 120                 125

Phe Met Asp Gln Val Val Trp Val Leu Glu Gly Ala Val Arg Ile Thr
    130                 135                 140

Glu Gly Glu Glu Val His Glu Leu Ser Thr Gly Asp Cys Leu Arg Phe
145                 150                 155                 160

Gly Pro Pro Arg Asp Thr Asp Phe Ala Asn Pro Thr Thr Val Ala Thr
                165                 170                 175
```

Arg Tyr Leu Val Ala Leu Asp Lys Arg Val Pro Arg Ala
            180                 185

<210> SEQ ID NO 3
<211> LENGTH: 382
<212> TYPE: PRT
<213> ORGANISM: Corynebacterium glutamicum

<400> SEQUENCE: 3

Met Asn Phe Tyr Pro Pro Ser Val Pro Ile Asn Pro Ala Trp Arg Pro
1               5                   10                  15

Pro Thr Val Thr Val Gln Ala Gly Arg Pro Ala Arg Thr Pro Gly Ala
            20                  25                  30

Pro Met Asn Pro Pro Ile Thr Leu Ser Ser Thr Tyr Val His Asp Ser
        35                  40                  45

Glu Lys Ala Tyr Gly Arg Asp Gly Asn Asp Gly Trp Gly Ala Phe Glu
    50                  55                  60

Ala Ala Met Gly Thr Leu Asp Gly Gly Phe Ala Val Ser Tyr Ser Ser
65                  70                  75                  80

Gly Leu Ala Ala Ala Thr Ser Ile Ala Asp Leu Val Pro Thr Gly Gly
                85                  90                  95

Thr Val Val Leu Pro Lys Ala Ala Tyr Tyr Gly Val Thr Asn Ile Phe
            100                 105                 110

Ala Arg Met Glu Ala Arg Gly Arg Leu Lys Val Arg Thr Val Asp Ala
        115                 120                 125

Asp Asn Thr Glu Glu Val Ile Ala Ala Gln Gly Ala Asp Val Val
    130                 135                 140

Trp Val Glu Ser Ile Ala Asn Pro Thr Met Val Val Ala Asp Ile Pro
145                 150                 155                 160

Ala Ile Val Asp Gly Val Arg Gly Leu Gly Val Leu Thr Val Val Asp
                165                 170                 175

Ala Thr Phe Ala Thr Pro Leu Arg Gln Arg Pro Leu Glu Leu Gly Ala
            180                 185                 190

Asp Ile Val Leu Tyr Ser Ala Thr Lys Leu Ile Gly Gly His Ser Asp
        195                 200                 205

Leu Leu Leu Gly Val Ala Val Cys Lys Ser Glu His His Ala Gln Phe
    210                 215                 220

Leu Ala Thr His Arg His Asp His Gly Ser Val Pro Gly Gly Leu Glu
225                 230                 235                 240

Ala Phe Leu Ala Leu Arg Gly Leu Tyr Ser Leu Ala Val Arg Leu Asp
                245                 250                 255

Arg Ala Glu Ser Asn Ala Ala Glu Leu Ser Arg Arg Leu Asn Ala His
            260                 265                 270

Pro Ser Val Thr Arg Val Asn Tyr Pro Gly Leu Pro Asp Asp Pro Gln
        275                 280                 285

His Glu Lys Ala Val Arg Val Leu Pro Ser Gly Cys Gly Asn Met Leu
    290                 295                 300

Ser Phe Glu Leu Asp Ala Thr Pro Glu Arg Thr Asp Glu Ile Leu Glu
305                 310                 315                 320

Ser Leu Ser Leu Leu Thr His Ala Thr Ser Trp Gly Gly Val Glu Thr
                325                 330                 335

Ala Ile Glu Arg Arg Thr Arg Arg Asp Ala Glu Val Val Ala Gly Val
            340                 345                 350

Pro Met Thr Leu Cys Arg Val Ser Val Gly Ile Glu Asp Val Glu Asp

```
              355                 360                 365
Leu Trp Glu Asp Leu Asn Ala Ser Ile Asp Lys Val Leu Gly
    370                 375                 380

<210> SEQ ID NO 4
<211> LENGTH: 32
<212> TYPE: DNA
<213> ORGANISM: Artificial Sequence
<220> FEATURE:
<223> OTHER INFORMATION: Synthetic DNA

<400> SEQUENCE: 4
gatctagaat tcaacatcgt ccgataggcc ag                           32

<210> SEQ ID NO 5
<211> LENGTH: 40
<212> TYPE: DNA
<213> ORGANISM: Artificial Sequence
<220> FEATURE:
<223> OTHER INFORMATION: Synthetic DNA

<400> SEQUENCE: 5
ggtctggtta ctggctacga atgcagacaa taatgtcgct                   40

<210> SEQ ID NO 6
<211> LENGTH: 32
<212> TYPE: DNA
<213> ORGANISM: Artificial Sequence
<220> FEATURE:
<223> OTHER INFORMATION: Synthetic DNA

<400> SEQUENCE: 6
gatctagaat tccgcttccg agaatcaata cc                           32

<210> SEQ ID NO 7
<211> LENGTH: 402
<212> TYPE: DNA
<213> ORGANISM: Artificial Sequence
<220> FEATURE:
<223> OTHER INFORMATION: Synthetic DNA

<400> SEQUENCE: 7
gatctagaat tcaacatcgt ccgataggcc agcgtctaat tcagcagcga tttcggcagc    60
aagcccagcg ccattaatca gagcggtgaa ataaacatgg ttcatgatta tgtcaggacg   120
gtaattagac ttatgaccag gtttaaggag gtcaccaggt tgaagccgcg ctattgttcc   180
gtggaaaagg gggccctgat ctagctgatt attcatcgca gtaagcgctt tcggtaggtg   240
ggtgaatcat cgtagtcttc cgagccccgt gacccgatcc gttttgtgca atccaatgct   300
actcccacag agcgggctac tttctctaaa aatgttctca tagtagataa aattgttctt   360
aaagcgacat tattgtctgc attcgtagcc agtaaccaga cc                     402

<210> SEQ ID NO 8
<211> LENGTH: 982
<212> TYPE: DNA
<213> ORGANISM: Artificial Sequence
<220> FEATURE:
<223> OTHER INFORMATION: Synthetic DNA

<400> SEQUENCE: 8
gatctagaat tcaacatcgt ccgataggcc agcgtctaat tcagcagcga tttcggcagc    60
aagcccagcg ccattaatca gagcggtgaa ataaacatgg ttcatgatta tgtcaggacg   120
```

-continued

```
gtaattagac ttatgaccag gtttaaggag gtcaccaggt tgaagccgcg ctattgttcc      180
gtggaaaagg gggccctgat ctagctgatt attcatcgca gtaagcgctt tcggtaggtg      240
ggtgaatcat cgtagtcttc cgagccccgt gacccgatcc gttttgtgca atccaatgct      300
actcccacag agcgggctac tttctctaaa aatgttctca tagtagataa aattgttctt      360
aaagcgacat tattgtctgc attcgtagcc agtaaccaga ccttcagtgt ttggttgcca      420
ctccagtgct ggggcgacat gatcagcgaa gttcttcagg atcgacgcgt tgatctcaac      480
acccatttgg ttgggggcgg tgagcatcaa ggtgtcggct tccatcacag ctttgtcttc      540
cttgagctgg tcgatgagtt catcgggact tccggcgtag ctgcgaccga acgtggatcg      600
ggtatcatcc aggattccta cttggtcacc gccttgtccc tgaagtccga aaagctcacg      660
gtcgcggtcg gtgacgatcg ggaagatgga cctggagaca gacacacgtg gggtccaatc      720
gtgtccggct tctttccaag cttggcggta gaacgcgatt tgatcggctt gcagatcccc      780
gaaggattgg ccggtggctt cggcgacgag ggtggagctc atcaagttaa cgccatcgcg      840
tgctgcttgt tcggcggtgt tgtgggaacc ggcgcccac caaatggatt tacgcaggtc       900
aggatcatgc gggaagatcg gcaggggagt gcccggatgg tagaggcgtg ggtattgatt      960
ctcggaagcg gaattctaga tc                                              982
```

NUCLEOTIDE SEQUENCES ENCODING O-SUCCINYLHOMOSERINE SULFHYDRYLASE

This application claims priority to U.S. Provisional Application 60/294,224 filed on May 31, 2001.

BACKGROUND OF THE INVENTION

1. Field of the Invention

The invention provides nucleotide sequences from coryneform bacteria which code for the metR and metZ genes and a process for the fermentative preparation of amino acids, in particular L-methionine, by attenuation of the metR and/or metZ gene.

2. Description of the Related Art

L-Amino acids, in particular methionine, are used in human medicine and in the pharmaceuticals industry, in the foodstuffs industry and very particularly in animal nutrition.

It is known that amino acids are prepared by fermentation from strains of coryneform bacteria, in particular *Corynebacterium glutamicum*. Because of their great importance, work is constantly being undertaken to improve the preparation process. Improvements to the process can relate to fermentation measures, such as stirring and supply of oxygen, or to the composition of the nutrient media, such as, the sugar concentration during the fermentation, or to the working up of the product by, for example, ion exchange chromatography, or to the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and which produce amino acids, such as e.g. L-methionine, are obtained in this manner.

Recombinant DNA techniques have also been employed for some years for improving of *Corynebacterium* strains which produce L-amino acids, by amplifying individual amino acid biosynthesis genes and investigating their effect on the amino acid production.

SUMMARY OF THE INVENTION

One object of the present invention is to provide new measures for improved fermentative preparation of amino acids, in particular L-methionine.

Where L-amino acids or amino acids are mentioned in the following, this means one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine.

When L-methionine or methionine are mentioned in the following, the salts, such as methionine hydrochloride or methionine sulfate are also meant.

The invention provides isolated polynucleotides from coryneform bacteria, which comprise the polynucleotide sequences which code for the metR and/or metZ genes, chosen from the group consisting of a) polynucleotide which is at least 70% identical to a polynucleotide which codes for a polypeptide which comprises the amino acid sequence of SEQ ID No. 2, b) polynucleotide which is at least 70% identical to a polynucleotide which codes for a polypeptide which comprises the amino acid sequence of SEQ ID No. 3, c) polynucleotide which codes for a polypeptide which comprises an amino acid sequence which is at least 70% identical to the amino acid sequence of SEQ ID No. 2, d) polynucleotide which codes for a polypeptide which comprises an amino acid sequence which is at least 70% identical to the amino acid sequence of SEQ ID No. 3, e) polynucleotide which is complementary to the polynucleotides of a), b) c) or d), and f) polynucleotide comprising at least 15 successive nucleotides of the polynucleotide sequence of a), b), c), d) or e), and the corresponding polypeptides according to a) or c) having the enzymatic activity of the transcription activator MetR and the polypeptides according to b) or d) having the enzymatic activity of O-succinylhomoserine sulfhydrylase (MetZ).

The invention also provides the above-mentioned polynucleotides, as DNAs which are capable of replication, comprising:

(i) the nucleotide sequence shown in SEQ ID No. 1, or (ii) at least one sequence which corresponds to sequence (i) within the range of the degeneration of the genetic code, or (iii) at least one sequence which hybridizes with the sequences complementary to sequences (i) or (ii), and optionally (iv) sense mutations of neutral function in (i).

The invention also provides:

a DNA which is capable of replication and comprises the nucleotide sequence as shown in SEQ ID No. 1, a polynucleotide that codes for a polypeptide which comprises the amino acid sequence as shown in SEQ ID No. 2 or SEQ ID No. 3, a vector containing parts of the polynucleotide according to the invention, but at least 15 successive nucleotides of the sequence claimed and coryneform bacteria in which the metR gene and/or the metZ gene is or are attenuated, in particular by deletion, insertion or base exchange.

The invention also provides polynucleotides which are obtained by screening a corresponding gene library of a coryneform bacterium, which comprises the complete gene or parts thereof by means of hybridization, with a probe which comprises the sequence of the polynucleotide according to the invention according to SEQ ID No. 1 or a fragment thereof, and isolation of the polynucleotide sequence mentioned.

DETAILED DESCRIPTION OF THE PREFERRED EMBODIMENTS

Polynucleotides according to the invention are suitable as hybridization probes for RNA, cDNA and DNA, in order to isolate, in the full length, nucleic acids, or polynucleotides or genes which code for the transcription activator MetR and/or O-succinylhomoserine sulfhydrylase or to isolate those nucleic acids or polynucleotides or genes which have a high similarity or homology with the sequence of the transcription activator MetR gene and/or that of the O-succinylhomoserine sulfhydrylase gene.

Polynucleotides according to the invention are furthermore suitable as primers with the aid of which DNA of genes that code for the transcription activator MetR and/or O-succinylhomoserine sulfhydrylase can be prepared by the polymerase chain reaction (PCR).

Such oligonucleotides that serve as probes or primers comprise at least 30, preferably at least 20, very particularly at least 15 successive nucleotides. Oligonucleotides which have a length of at least 40 or 50 nucleotides are also suitable. Oligonucleotides with a length of at least 100, 150, 200, 250 or 300 nucleotides are optionally also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least 70%, preferably at least 80% and in particular at least 90% to 95% identical to the polynucleotide according to SEQ ID No. 1 or a fragment prepared therefrom.

The polypeptides according to the invention include the polypeptides according to SEQ ID No. 2 and SEQ ID No. 3, in particular those with the biological activity of the transcription activator MetR and of O-succinylhomoserine sulfhydrylase, and also those which are at least 70%, preferably at least 80%, and in particular which are at least 90% to 95% identical to the polypeptides according to SEQ ID No. 2 and SEQ ID No. 3 and have the activities mentioned.

"Polypeptides" are understood as meaning peptides or proteins which comprise two or more amino acids bonded via peptide bonds.

The invention moreover provides a process for the fermentative preparation of amino acids, in particular methionine, using coryneform bacteria which in particular already produce the amino acids, and in which the nucleotide sequences which code for the metR gene and/or for the metZ gene are attenuated, in particular eliminated or expressed at a low level.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

By attenuation measures, the activity or concentration of the corresponding protein is in general reduced to 0 to 50%, 0 to 25%, 0 to 10% or 0 to 5% of the activity or concentration of the wild-type protein.

The microorganisms which the present invention provides can prepare L-amino acids, in particular methionine, from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum* (*C. glutamicum*), are in particular the known wild-type strains

*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020 or L-amino acid-producing mutants or strains prepared therefrom, such as, for example, the L-methionine-producing strain

*Corynebacterium glutamicum* ATCC21608.

The new metR and metZ genes from *C. glutamicum* which code for the transcription activator MetR and the enzyme O-succinylhomoserine sulfhydrylase have been isolated.

To isolate the metR gene, the metZ gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie (Verlag Chemie, Weinheim, Germany, 1990), or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in λ vectors by Kohara et al. (Cell 50, 495–508 (1987)). Bathe et al. (Molecular and General Genetics, 252:255–265, 1996) describe a gene library of *C. glutamicum* ATCC13032, which was set up with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575).

Börmann et al. (Molecular Microbiology 6(3), 317–326) (1992)) in turn describe a gene library of *C. glutamicum* ATCC13032 using the cosmid pHC79 (Hohn and Collins, Gene 11, 291–298 (1980)). To prepare a gene library of *C. glutamicum* in *E. coli* it is also possible to use plasmids such as pBR322 (Bolivar, Life Sciences, 25, 807–818 (1979)) or pUC9 (Vieira et al., 1982, Gene, 19:259–268). Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645–4649). The long DNA fragments cloned with the aid of cosmids can in turn be subcloned in the usual vectors suitable for sequencing and then sequenced, as is described e.g. by Sanger et al. (Proceedings of the National Academy of Sciences of the United States of America, 74:5463–5467, 1977).

The resulting DNA sequences can then be investigated with known algorithms or sequence analysis programs, such as that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The new DNA sequence of *C. glutamicum* which codes for the metR and metZ genes and which, as SEQ ID No. 1, is a constituent of the present invention has been found. The amino acid sequence of the corresponding proteins has furthermore been derived from the present DNA sequence by the methods described above. The resulting amino acid sequences of the metR and metZ gene products are shown in SEQ ID No. 2 and 3.

Coding DNA sequences which result from SEQ ID No. 1 by the degeneracy of the genetic code are also a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. they are of neutral function.

It is furthermore known that changes at the N and/or C terminus of a protein must not substantially impair and may even stabilize the function thereof. Information in this context can be found in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID No. 2 or SEQ ID No. 3 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found in the handbook "The DIG System Users Guide for Filter Hybridization" from Boehringer Mannheim GmbH (Mannheim, Germany, 1993) and in Liebl et al. (International Journal of Systematic Bacteriology (1991) 41: 255–260). The hybridization takes place under stringent conditions, i.e. only hybrids in which the probe and target sequence, i.e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996).

A 5×SSC buffer at a temperature of approx. 50–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995) a temperature of approx. 50–68° C. being established. It is optionally possible to lower the salt concentration to 0.1×SSC. Polynucleotide fragments which are, for example, at least 70% or at least 80% or at least 90% to 95% identical to the sequence of the probe employed can be isolated by increasing the hybridization temperature stepwise from 50 to 68° C. in steps of approx. 1–2° C. Further instructions on hybridization are obtainable on the market in the form of so-called kits (e.g. DIG Easy Hyb from Roche Diagnostics GmbH, Mannheim, Germany, Catalogue No. 1603558).

Instructions for amplification of DNA sequences with the aid of the polymerase chain reaction (PCR) can be found in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994).

It has been found that coryneform bacteria produce amino acids, in particular L-methionine, in an improved manner after attenuation of the metR and/or metZ gene.

To achieve an attenuation, either the expression of the metR and/or of the metZ gene or the catalytic properties of the enzyme proteins can be reduced or eliminated. The two measures can optionally be combined.

The reduction in gene expression can take place by suitable culturing or by genetic modification (mutation) of the signal structures of gene expression. Signal structures of gene expression are, for example, repressor genes, activator genes, operators, promoters, attenuators, ribosome binding sites, the start codon and terminators. The expert can find information on this e.g. in the patent application WO 96/15246, in Boyd and Murphy (Journal of Bacteriology 170: 5949 (1988)), in Voskuil and Chambliss (Nucleic Acids Research 26: 3548 (1998), in Jensen and Hammer (Biotechnology and Bioengineering 58: 191 (1998)), in Pátek et al. (Microbiology 142: 1297 (1996)), Vasicova et al. (Journal of Bacteriology 181: 6188 (1999)) and in known textbooks of genetics and molecular biology, such as e.g. the textbook by Knippers ("Molekulare Genetik", 6th edition, Georg Thieme Verlag, Stuttgart, Germany, 1995) or that by Winnacker ("Gene und Klone", VCH Verlagsgesellschaft, Weinheim, Germany, 1990).

Mutations which lead to a change or reduction in the catalytic properties of enzyme proteins are known from the prior art; examples which may be mentioned are the works by Qiu and Goodman (Journal of Biological Chemistry 272: 8611–8617 (1997)), Sugimoto et al. (Bioscience Biotechnology and Biochemistry 61: 1760–1762 (1997)) and Möckel ("Die Threonindehydratase aus *Corynebacterium glutamicum*: Aufhebung der allosterischen Regulation und Struktur des Enzyms", Reports from the Jülich Research Center, Jül-2906, ISSN09442952, Jülich, Germany, 1994). Summarizing descriptions can be found in known textbooks of genetics and molecular biology, such as e.g. that by Hagemann ("Allgemeine Genetik", Gustav Fischer Verlag, Stuttgart, 1986).

Possible mutations are transitions, transversions, insertions and deletions. Depending on the effect of the amino acid exchange on the enzyme activity, "missense mutations" or "nonsense mutations" are referred to. Insertions or deletions of at least one base pair in a gene lead to "frame shift mutations", as a consequence of which incorrect amino acids are incorporated or translation is interrupted prematurely. Deletions of several codons typically lead to a complete loss of the enzyme activity. Instructions on generation of such mutations are prior art and can be found in known textbooks of genetics and molecular biology, such as e.g. the textbook by Knippers ("Molekulare Genetik", 7th edition, Georg Thieme Verlag, Stuttgart, Germany, 1997), that by Winnacker ("Gene und Klone", VCH Verlagsgesellschaft, Weinheim, Germany, 1999) or that by Hagemann ("Allgemeine Genetik", 4th edition, Gustav Fischer Verlag, Stuttgart, 1999).

A common method of mutating genes of *C. glutamicum* is the method of "gene disruption" and "gene replacement" described by Schwarzer and Puhler (Bio/Technology 9, 84–87 (1991)).

In the method of gene disruption a central part of the coding region of the gene of interest is cloned in a plasmid vector which can replicate in a host (typically *E. coli*), but not in *C. glutamicum*. Possible vectors are, for example, pSUP301 (Simon et al., Bio/Technology 1, 784–791 (1983)), pK18mob or pK19mob (Schäfer et al., Gene 145, 69–73 (1994)), pK18mobsacB or pK19mobsacB (Jäger et al., Journal of Bacteriology 174: 5462–65 (1992)), pGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, The Netherlands; Bernard et al., Journal of Molecular Biology, 234: 534–541 (1993)) or pEM1 (Schrumpf et al, 1991, Journal of Bacteriology 173:4510–4516). The plasmid vector which contains the central part of the coding region of the gene is then transferred into the desired strain of C. glutamicum by conjugation or transformation. The method of conjugation is described, for example, by Schafer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross over" event, the coding region of the gene in question is interrupted by the vector sequence and two incomplete alleles are obtained, one lacking the 3' end and one lacking the 5' end. This method has been used, for example, by Fitzpatrick et al. (Applied Microbiology and Biotechnology 42, 575–580 (1994)) to eliminate the recA gene of C. glutamicum.

In the method of "gene replacement", a mutation, such as e.g. a deletion, insertion or a base exchange, is established in vitro in the gene of interest. The allele prepared is in turn cloned in a vector which is not replicative for C. glutamicum and this is then transferred into the desired host of C. glutamicum by transformation or conjugation. After homologous recombination by means of a first "cross over" event which effects integration and a suitable second "cross-over" event which effects excision in the target gene or in the target sequence, the incorporation of the mutation or of the allele is achieved. This method was used, for example, by Peters-Wendisch et al.(Microbiology 144, 915–927 (1998)) to eliminate the pyc gene of C. glutamicum by a deletion.

A deletion, insertion or a base exchange can be incorporated into the metR gene or the metZ gene in this manner.

In addition, it may be advantageous for the production of L-amino acids, in particular L-methionine, to enhance, in particular to over-express, one or more enzymes of the particular biosynthesis pathway, of glycolysis, of anaplerosis, of the citric acid cycle or of amino acid export, in addition to attenuation of the metR gene and/or of the metZ gene.

The term "enhancement" in this connection describes the increase in the intracellular activity of one or more enzymes (proteins) in a microorganism which are coded by the corresponding DNA, for example by increasing the number of copies of the gene or genes, using a potent promoter or using a gene or allele which codes for a corresponding enzyme (protein) having a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on the starting microorganism.

Thus, for the preparation of L-methionine, one or more genes chosen from the group consisting of the gap gene which codes for glyceraldehyde 3-phosphate dehydrogenase (Eikmanns (1992), Journal of Bacteriology 174:6076–6086), the tpi gene which codes for triose phosphate isomerase (Eikmanns (1992), Journal of Bacteriology 174:6076–6086), the pgk gene which codes for 3-phosphoglycerate kinase (Eikmanns (1992), Journal of Bacteriology 174:6076–6086), the pyc gene which codes for pyruvate carboxylase (Peters-Wendisch et al.(Microbiology 144, 915–927 (1998)), the lysC gene which codes for a feed-back resistant aspartate kinase (Accession No.P26512), the metA gene which codes for homoserine O-acetyltransferase (ACCESSION Number AF052652; EP-B-0387527; EP-A-0699759), the metB gene which codes for cystathionine gamma-synthase (ACCESSION Number AF126953), the aecD gene which codes for cystathionine gamma-lyase (ACCESSION Number M89931), the glyA gene which codes for serine hydroxymethyl-transferase (JP-A-08107788), the metY gene which codes for O-acetylhomoserine sulf-hydrylase (DSM 13556)

can be enhanced, in particular over-expressed.

It may furthermore be advantageous for the production of L-methionine, in addition to the attenuation of the metR and/or metZ gene, for one or more genes chosen from the group consisting of the thrB gene which codes for homoserine kinase (ACCESSION Number P08210), the ilvA gene which codes for threonine dehydratase (ACCESSION Number Q04513), the thrC gene which codes for threonine synthase (ACCESSION Number P23669), the ddh gene which codes for meso-diaminopimelate D-dehydrogenase (ACCESSION Number Y00151)

the pck gene which codes for phosphoenol pyruvate carboxykinase (DE 199 50 409.1; DSM 13047), the pgi gene which codes for glucose 6-phosphate isomerase (U.S. Ser. No. 09/396,478; DSM 12969), the poxB gene which codes for pyruvate oxidase (DE: 1995 1975.7) to be attenuated, in particular for the expression thereof to be reduced.

In addition to attenuation of the metR gene and/or of the metZ gene it may furthermore be advantageous, for the production of amino acids, in particular L-methionine, to eliminate undesirable side reactions (Nakayama: "Breeding of Amino Acid Producing Micro-organisms", in: Overproduction of Microbial Products, Krumphanzl, Sikyta, Vanek (eds.), Academic Press, London, UK, 1982).

The invention also provides the microorganisms prepared according to the invention, and these can be cultured continuously or discontinuously in the batch process (batch culture) or in the fed batch (feed process) or repeated fed batch process (repetitive feed process) for the purpose of production of L-amino acids, in particular L-methionine. A summary of known culture methods is described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as, for example, soya oil, sunflower oil, groundnut oil and coconut fat, fatty acids, such as, for example, palmitic acid, stearic acid and linoleic acid, alcohols, such as, for example, glycerol and ethanol, and organic acids, such as, for example, acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Organic and inorganic sulfur-containing compounds, such as, for example, sulfides, sulfites, sulfates and thiosulfates, can be used as a source of sulfur, in particular for the preparation of methionine.

Phosphoric acid, potassium dihydrogen phosphate or dipotassium hydrogen phosphate or the corresponding sodium-containing salts can be used as the source of phosphorus. The culture medium must furthermore comprise salts of metals, such as, for example, magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as, for example, fatty acid polyglycol esters, can be employed to control the development of foam. Suitable substances having a selective action, such as, for example, antibiotics, can be added to the medium to maintain the stability of plasmids. To maintain aerobic conditions, oxygen or oxygen-containing gas mixtures, such as, for example, air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

The fermentation broths obtained in this way, in particular containing L-methionine, usually have a dry weight of 7.5 to 25 wt. % and contain L-methionine. It is furthermore also advantageous if the fermentation is conducted in a sugar-limited procedure at least at the end, but in particular over at least 30% of the duration of the fermentation. That is to say, the concentration of utilizable sugar in the fermentation medium is reduced to $\geq 0$ to 3 g/l during this period.

The fermentation broth prepared in this manner, in particular containing L-methionine, is then further processed. Depending on requirements, the all or some of the biomass can be removed from the fermentation broth by separation methods, such as centrifugation, filtration, decanting or a combination thereof, or it can be left completely in. This broth is then thickened or concentrated by known methods, such as with the aid of a rotary evaporator, thin film evaporator, falling film evaporator, by reverse osmosis, or by nanofiltration. This concentrated fermentation broth can then be worked up by methods of freeze drying, spray drying, spray granulation or by other processes to give a preferably free-flowing, finely divided powder.

This free-flowing, finely divided powder can then in turn by converted by suitable compacting or granulating processes into a coarse-grained, readily free-flowing, storable and largely dust-free product. In the granulation or compacting it is advantageous to employ conventional organic or inorganic auxiliary substances or carriers, such as starch, gelatin, cellulose derivatives or similar substances, such as are conventionally used as binders, gelling agents or thickeners in foodstuffs or feedstuffs processing, or further substances, such as, for example, silicas, silicates or stearates.

"Free-flowing" is understood as meaning powders which flow unimpeded out of the vessel with the opening of 5 mm (millimeters) of a series of glass outflow vessels with outflow openings of various sizes (Klein, Seifen, Öle, Fette, Wachse 94, 12 (1968)).

As described here, "finely divided" means a powder with a predominant content (>50%) having a particle size of 20 to 200 $\mu$m diameter. "Coarse-grained" means products with a predominant content (>50%) having a particle size of 200 to 2000 $\mu$m diameter. In this context, "dust-free" means that the product contains only small contents (<5%) having particle sizes of less than 20 $\mu$m diameter. The particle size determination can be carried out with methods of laser diffraction spectrometry. The corresponding methods are described in the textbook on "Teilchengrößenmessung in der Laborpraxis" by R. H. Müller and R. Schuhmann, Wissenschaftliche Verlagsgesellschaft Stuttgart (1996) or in the textbook "Introduction to Particle Technology" by M. Rhodes, Verlag Wiley & Sons (1998).

"Storable" in the context of this invention means a product which can be stored for up to 120 days, preferably up to 52 weeks, particularly preferably 60 months, without a substantial loss (<5%) of methionine occurring.

Alternatively, however, the product can be absorbed on to an organic or inorganic carrier substance which is known and conventional in feedstuffs processing, for example, silicas, silicates, grits, brans, meals, starches, sugars or others, and/or mixed and stabilized with conventional thickeners or binders. Use examples and processes in this context are described in the literature (Die Mühle +Mischfuttertechnik 132 (1995) 49, page 817).

Finally, the product can be brought into a state in which it is stable to digestion by animal stomachs, in particular the stomach of ruminants, by coating processes ("coating") using film-forming agents, such as, for example, metal carbonates, silicas, silicates, alginates, stearates, starches, gums and cellulose ethers, as described in DE-C-4100920.

If the biomass is separated off during the process, further inorganic solids, for example added during the fermentation, are in general removed. In addition, the animal feedstuffs additive according to the invention comprises at least the predominant proportion of the further substances, in particular organic substances, which are formed or added and are present in solution in the fermentation broth, where these have not been separated off by suitable processes.

In one aspect of the invention, the biomass can be separated off to the extent of up to 70%, preferably up to 80%, preferably up to 90%, preferably up to 95%, and particularly preferably up to 100%. In another aspect of the invention, up to 20% of the biomass, preferably up to 15%, preferably up to 10%, preferably up to 5%, particularly preferably no biomass is separated off.

These organic substances include organic by-products which are optionally produced, in addition to the L-methionine, and optionally discharged by the microorganisms employed in the fermentation. These include L-amino acids chosen from the group consisting of L-lysine, L-valine, L-threonine, L-alanine or L-tryptophan. They include vitamins chosen from the group consisting of vitamin B1 (thiamine), vitamin B2 (riboflavin),vitamin B5 (pantothenic acid), vitamin B6 (pyridoxine), vitamin B12 (cyanocobalamin), nicotinic acid/nicotinamide and vitamin E (tocopherol). They also include organic acids which carry one to three carboxyl groups, such as, acetic acid, lactic acid, citric acid, malic acid or fumaric acid. Finally, they also include sugars, for example, trehalose. These compounds are optionally desired if they improve the nutritional value of the product.

These organic substances, including L-methionine and/or D-methionine and/or the racemic mixture D,L-methionine, can also be added, depending on requirements, as a concentrate or pure substance in solid or liquid form during a suitable process step. These organic substances mentioned can be added individually or as mixtures to the resulting or concentrated fermentation broth, or also during the drying or granulation process. It is likewise possible to add an organic substance or a mixture of several organic substances to the fermentation broth and a further organic substance or a further mixture of several organic substances during a later process step, for example granulation.

The product described above is suitable as a feedstuffs additive, i.e. feed additive, for animal nutrition.

The L-methionine content of the animal feedstuffs additive is conventionally 1 wt. % to 80 wt. %, preferably 2 wt. % to 80 wt. %, particularly preferably 4 wt. % to 80 wt. %, and very particularly preferably 8 wt. % to 80 wt. %, based on the dry weight of the animal feedstuffs additive. Contents of 1 wt. % to 60 wt. %, 2 wt. % to 60 wt. %, 4 wt. % to 60 wt. %, 6 wt. % to 60 wt. %, 1 wt. % to 40 wt. %, 2 wt. % to 40 wt. % or 4 wt. % to 40 wt. % are likewise possible. The water content of the feedstuffs additive is conventionally up to 5 wt. %, preferably up to 4 wt. %, and particularly preferably less than 2 wt. %.

The invention also provides a process for the preparation of an L-methionine-containing animal feedstuffs additive from fermentation broths, which comprises the steps a) culture and fermentation of an L-methionine-producing microorganism in a fermentation medium;

b) removal of water from the L-methionine-containing fermentation broth (concentration);

c) removal of an amount of 0 to 100 wt. % of the biomass formed during the fermentation; and d) drying of the fermentation broth obtained according to a) and/or b) to obtain the animal feedstuffs additive in the desired powder or granule form.

If desired, one or more of the following steps can furthermore be carried out in the process according to the invention:

e) addition of one or more organic substances, including L-methionine and/or D-methionine and/or the racemic mixture D,L-methionine, to the products obtained according to a), b) and/or c);

f) addition of auxiliary substances chosen from the group consisting of silicas, silicates, stearates, grits and bran to the substances obtained according to a) to d) for stabilization and to increase the storability; or g) conversion of the substances obtained according to a) to e) into a form stable to an animal stomach, in particular rumen, by coating with film-forming agents.

Methods for the determination of L-amino acids are known from the prior art. The analysis of L-methionine can be carried out by ion exchange chromatography with subsequent ninhydrin derivation, as described by Spackman et al. (Analytical Chemistry, 30, (1958), 1190).

The process according to the invention is used for the fermentative preparation of amino acids, in particular L-methionine.

The present invention is explained in more detail in the following with the aid of embodiment examples.

The isolation of plasmid DNA from *Escherichia coli* and all techniques of restriction, Klenow and alkaline phosphatase treatment were carried out by the method of Sambrook et al. (Molecular Cloning. A Laboratory Manual (1989) Cold Spring Harbor Laboratory Press, Cold Spring Harbor, N.Y., USA). Methods for transformation of *Escherichia coli* are also described in this handbook.

The composition of the usual nutrient media, such as LB or TY medium, can also be found in the handbook by Sambrook et al.

EXAMPLE 1

Preparation of a Genomic Cosmid Gene Library from *Corynebacterium glutamicum* ATCC 13032

Chromosomal DNA from *Corynebacterium glutamicum* ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Diagnostics GmbH, Mannheim, Germany, Product Description SAP, Code no. 1758250). The DNA of the cosmid vector SuperCos1 (Wahl et al. (1987) Proceedings of the National Academy of Sciences USA 84:2160–2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no.27-0870-04). The ligation mixture was then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Research 16:1563–1575) the cells were taken up in 10 mM MgSO$_4$ and mixed with an aliquot of the phage suspension. The infection and titering of the cosmid library were carried out as described by Sambrook et al. (1989, Molecular Cloning: A Laboratory Manual, Cold Spring Harbor), the cells being plated out on LB agar (Lennox, 1955, Virology, 1:190) with 100 mg/l ampicillin. After incubation overnight at 37° C., recombinant individual clones were selected.

EXAMPLE 2

Isolation and Sequencing of the metR and metZ Genes

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Diagnostics GmbH, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343–7) into the E. coli strain DH5aMCR (Grant, 1990, Proceedings of the National Academy of Sciences U.S.A., 87:4645–4649) and plated out on LB agar (Lennox, 1955, Virology, 1:190) with 50 mg/l zeocin.

The plasmid preparation of the recombinant clones was carried out with Biorobot 9600 (Product No. 900200, Qiagen, Hilden, Germany). The sequencing was carried out by the dideoxy chain termination method of Sanger et al. (1977, Proceedings of the National Academy of Sciences U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 3771" sequencer from PE Applied Biosystems (Weiterstadt, Germany).

The raw sequence data obtained were then processed using the Staden program package (1986, Nucleic Acids Research, 14:217–231) version 97-0. The individual sequences of the pZero1 derivatives were assembled to a continuous contig. The computer-assisted coding region analysis was prepared with the XNIP program (Staden, 1986, Nucleic Acids Research, 14:217–231).

The resulting nucleotide sequence is shown in SEQ ID No. 1. Analysis of the nucleotide sequence showed two open reading frames of 567 base pairs and 1146 base pairs, which were called the metR gene and metZ gene. The metR gene codes for a protein of 189 amino acids, the metZ gene codes for a protein of 382 amino acids.

EXAMPLE 3

Deletion of the metR and metZ Genes in C. glutamicum ATCC13032

For this, chromosomal DNA was isolated from the strain ATCC13032 by the method of Tauch et al. (Plasmid 33:168–179 (1995)). On the basis of the sequences of the metR and metZ genes known for C. glutamicum from example 2, the oligonucleotides described below were chosen for generation of the metR-metZ deletion allele by means of the polymerase chain reaction (PCR) by the gene Soeing method (Horton, Molecular Biotechnology 3: 93–98 (1995)).

orfR 20 (see also SEQ ID No. 4): 5'-GAT CTA GAA TTC AAC ATC GTC CGA TAG GCC AG-3' orfRmetZ del (see also SEQ ID No. 5): 5'-GGT CTG GTT ACT GGC TAC GAA TGC AGA CAA TAA TGT CGC T-3' metZ 21 (see also SEQ ID No. 6): 5'-GAT CTA GAA TTC CGC TTC CGA GAA TCA ATA CC-3'

The primers shown were synthesized by MWG Biotech (Ebersberg, Germany) and the PCR reaction was carried out using Pfu polymerase (Stratagene, Product. No. 600135, La Jolla, USA) and a PTC 100 Thermocycler (MJ Research Inc., Waltham, USA).

The primers orfR 20 and metZ 21 contain in each case an inserted cleavage site for the restriction enzyme EcoRI, which are marked by underlining in the nucleotide sequence shown above. The primer orfRmetZ del is composed of two regions of the nucleotide sequence, one of which bonds in the "upstream" region of metR and includes the first two nucleotides of the start codon ATG, and the other bonds after the stop codon of metZ in the "downstream" region thereof.

In a first PCR reaction, by means of the primers orfR 20 and orfRmetZ del an amplification product 402 bp in size was produced which contains the "upstream" region of the met R gene including the first two nucleotides of the start codon ATG, and additionally a 20 bp extension, appended with the oligonucleotide orfRmetZ del, which corresponds to a part of the nucleotide sequence of the "downstream" region of metZ. The amplification product was isolated from the agarose gel with the QiaExII Gel Extraction Kit (Product No. 20021, Qiagen, Hilden, Germany). It was called metRmetZ del fragment 1 and is shown in SEQ ID No. 7.

In a second PCR reaction the metRmetZ deletion derivative 982 bp in size was produced with the primer metZ 21 and the purified amplification product metRmetZ del fragment 1, which can bond by means of the 20 bp extension from the oligonucleotide orfRmetZ del in the "downstream" region of metZ to the DNA and function there as a primer. It comprises, between the two EcoRI cleavage sites appended to the primers, 368 bp of the "upstream region" of the metR gene, the first two nucleotides of the start codon ATG and 588 bp of the "downstream" region of the metZ gene, starting with the fourth nucleotide after the stop codon of the metZ gene.

It was called metRmetZ del fragment 2 and is shown in SEQ ID No. 8.

EXAMPLE 4

Deletion Mutagenesis of the metR and metZ Genes in C. glutamicum ATCC13032

The 982 bp metRmetZ deletion derivative obtained in example 3 was incorporated by means of deletion mutagenesis with the aid of the sacB system described by Schafer et al., Gene, 14, 69–73 (1994) into the chromosome of C. glutamicum. This system enables the expert to identify or select allele exchanges which take place by homologous recombination.

1. Construction of the exchange vector pK18mobsacBdeltametRmetZ

The metRmetZ deletion derivative 982 bp in size obtained in example 3 was cleaved with the restriction endonuclease EcoRI and then isolated from the agarose gel with the QiaExII Gel Extraction Kit (Product No. 20021, Qiagen, Hilden, Germany) and used for ligation with the mobilizable cloning vector pK18mobsacB described by Schäfer et al., Gene, 14, 69–73 (1994). This was cleaved beforehand with the restriction enzyme EcoRI, subsequently dephosphorylated with shrimp alkaline phosphatase (Roche Diagnostics GmbH, Mannheim, Germany, Product Description SAP, Product No. 1758250) and then mixed with the metRmetZ deletion derivative, and the mixture was treated with T4 DNA ligase (Amersham-Pharmacia, Freiburg, Germany).

The E. coli strain S17-1 (Simon et al., Bio/Technologie [Bio/Technology] 1: 784–791, 1993) was then electroporated with the ligation batch (Hanahan, In. DNA cloning. A practical approach. Vol.1. ILR-Press, Cold Spring Harbor, New York, 1989). Selection of plasmid-carrying cells was made by plating out the transformation batch on LB agar (Sambrock et al., Molecular Cloning: A Laboratory Manual, $2^{nd}$ Ed., Cold Spring Harbor, N.Y., 1989), which had been supplemented with 25 mg/l kanamycin.

Plasmid DNA was isolated from a transformant with the aid of the QIAprep Spin Miniprep Kit from Qiagen and the cloned 1rp deletion allele was verified by means of sequencing by MWG Biotech (Ebersberg, Germany).

Figure 1:
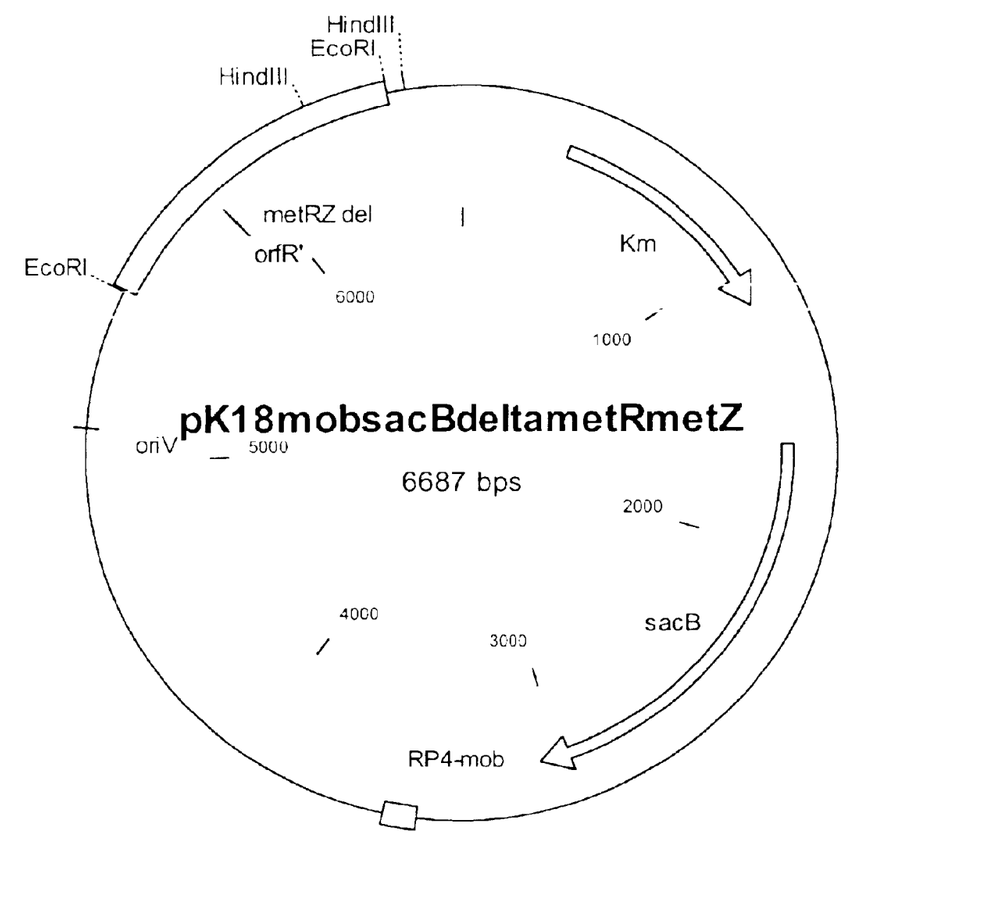
FIG. 1 shows plasmid pK18mobsacBdeltametRmetZ.

The plasmid was called pK18mobsacBdeltametRmetZ and is shown in FIG. 1.

EXAMPLE 5

Deletion Mutagenesis of the metR and metZ Genes in the *C. glutamicum* Strain ATCC13032

The vector pK18mobsacBdeltametRmetZ mentioned in example 4 was electroporated by the electroporation method of Tauch et al.,(1989 FEMS Microbiology Letters 123: 343–347) in the strain *C. glutamicum* ATCC13032. The vector cannot replicate independently in ATCC13032 and is retained in the cell only if it has integrated into the chromosome. Selection of clones with integrated pK18mobsacBdeltametRmetZ was carried out by plating out the electroporation batch on LB agar (Sambrook et al., Molecular Cloning: A Laboratory Manual, $2^{nd}$ Ed., Cold Spring Harbor, N.Y., 1989), which had been supplemented with 15 mg/l kanamycin. Clones which had grown on were plated out on LB agar plates with 25 mg/l kanamycin and incubated for 16 hours at 33° C. To achieve excision of the plasmid together with the complete chromosomal copy of the metR and metZ genes, the clones were incubated unselectively overnight in LB medium and then cultured on LB agar with 10% sucrose.

The plasmid pK18mobsacB contains a copy of the sacB gene, which converts sucrose into levan sucrase, which is toxic to *C. glutamicum*. Only those clones in which the pK18mobsacBdeltametRmetZ integrated has been excised again therefore grow on LB agar with sucrose. In the excision, together with the plasmid either the complete chromosomal copy of the metR and metZ genes can be excised, or the metRmetZ deletion derivative. To demonstrate that the metR and metZ genes are deleted in the chromosome, the plasmid pK18mobsacBdeltametRmetZ was marked by the method of "The DIG System Users Guide for Filter Hybridization" of Boehringer Mannheim GmbH (Mannheim, Germany, 1993) using the DIG hybridization kit from Boehringer. Chromosomal DNA of a potential deletion mutant was isolated by the method of Eikmanns et al. (Microbiology 140: 1817–1828 (1994)) and in each case cleaved with the restriction enzymes HindIII and EcoRI in separate batches.

The fragments formed were separated by agarose gel electrophoresis and hybridized at 68° C. with the Dig hybridization kit from Boehringer. With the aid of the fragments formed, it could be shown that the strain ATCC13032 has lost its copies of the metR and metZ genes, and instead the region from the 3rd nucleotide of the metR gene up to and including the 3rd nucleotide after the metZ gene is deleted.

The strain was called *C. glutamicum* ATCC13032deltametRmetZ.

EXAMPLE 6

Preparation of Methionine with the Strain *C. glutamicum* ATCC13032deltametRmetZ The *C. glutamicum* strain ATCC13032deltametRmetZ obtained in example 4 was cultured in a nutrient medium suitable for the production of methionine and the methionine content in the culture supernatant was determined.

For this, the strain was first incubated on a brain-heart agar plate for 24 hours at 33° C. Starting from this agar plate culture, a preculture was seeded (10 ml medium in a 100 ml conical flask). The medium MM was used as the medium for the preculture.

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.01 mg/l |
| Vitamin B12 (sterile-filtered) | 0.02 mg/l |
| Thiamine * HCl (sterile-filtered) | 0.2 mg/l |
| $CaCO_3$ | 25 g/l |

The CSL, MOPS and the salt solution were brought to pH 7 with aqueous ammonia and autoclaved. The sterile substrate and vitamin solutions were then added, as well as the $CaCO_3$ autoclaved in the dry state.

The preculture was incubated for 16 hours at 33° C. at 240 rpm on a shaking machine. A main culture was seeded from this preculture such that the initial OD (660 nm) of the main culture was 0.1. Medium MM was also used for the main culture. Culturing is carried out in a 10 ml volume in a 100 ml conical flask with baffles. Culturing was carried out at 33° C. and 80% atmospheric humidity.

After 72 hours, the OD was determined at a measurement wavelength of 660 nm with a Biomek 1000 (Beckmann Instruments GmbH, Munich). The amount of methionine formed was determined with an amino acid analyzer from Eppendorf-BioTronik (Hamburg, Germany) by ion exchange chromatography and post-column derivation with ninhydrin detection.

The result of the experiment is shown in table 1.

TABLE 1

| Strain | OD (660 nm) | Methionine mg/l |
|---|---|---|
| ATCC13032 | 11.3 | 1.5 |
| ATCC13032deltametRmetZ | 12.0 | 9.4 |

Brief Description of the Figure:

FIG. 1: Map of the plasmid pK18mobsacBdeltametRmetZ.

The abbreviations and designations used have the following meaning:

| | |
|---|---|
| sacB | sacB gene |
| oriV | ColE1-similar origin from pMB1 |
| KmR | Kanamycin resistance |
| HindIII | Cleavage site of the restriction enzyme HindIII |
| EcoRI | Cleavage site of the restriction enzyme EcoRI |
| RP4mob | RP4 mobilization site |
| orfR | Nucleotides A and T of the start codon of metR |
| metRmetZ del | Cloned deletion derivative for metR and metZ |

This disclosure is based on priority documents DE 100 43 335.9, DE 101 09 688.7 and U.S. Ser. No. 60/294,224, each incorporated by reference.

Obviously, numerous modifications of the invention are possible in view of the above teachings. Therefore, within the scope of the appended claims, the invention may be practiced otherwise than as specifically described herein.

What is claimed is:

1. An isolated polynucleotide fragment comprising:
   (a) a nucleotide sequence that encodes a protein which comprises the amino acid sequence of SEQ ID NO:2 or
   (b) a nucleotide sequence which is fully complimentary to (a).
2. The isolated polynucleotide fragment of claim 1, which is capable of replication in coryneform bacteria.
3. The isolated polynucleotide fragment of claim 1, wherein the polynucleotide fragment is RNA.
4. The isolated polynucleotide fragment of claim 1, which comprises a nucleotide sequence that encodes a protein which comprises the amino acid sequence of SEQ ID NO:2.
5. The isolated polynucleotide fragment of claim 1, which comprises the nucleotide sequence of SEQ ID NO:1.
6. A vector comprising the isolated polynucleotide fragment of claim 1.
7. A vector comprising the isolated polynucleotide fragment of claim 4.
8. A vector comprising the isolated polynucleotide fragment of claim 5.
9. An *Escherichia coli* cell transformed with the isolated polynucleotide fragment of claim 1.
10. An *Escherichia coli* cell transformed with the isolated polynucleotide fragment of claim 4.
11. An *Escherichia coli* cell transformed with the isolated polynucleotide fragment of claim 5.

* * * * *